(12) United States Patent
Mance et al.

(10) Patent No.: US 8,281,791 B2
(45) Date of Patent: Oct. 9, 2012

(54) METHOD AND APPARATUS FOR EAR PROTECTION

(76) Inventors: Marilyn J. Mance, Pittsburgh, PA (US); Frank R. Mance, Pittsburgh, PA (US)

(*) Notice: Subject to any disclaimer, the term of this patent is extended or adjusted under 35 U.S.C. 154(b) by 183 days.

(21) Appl. No.: 12/719,963

(22) Filed: Mar. 9, 2010

(65) Prior Publication Data

US 2010/0229877 A1 Sep. 16, 2010

Related U.S. Application Data

(60) Provisional application No. 61/209,977, filed on Mar. 13, 2009.

(51) Int. Cl.
*A61F 11/00* (2006.01)
*A61F 13/00* (2006.01)

(52) U.S. Cl. .......................... 128/864; 424/443

(58) Field of Classification Search .................. 128/864; 424/443, 445, 447, 448
See application file for complete search history.

(56) References Cited

U.S. PATENT DOCUMENTS 2,738,514 A * 3/1956 Gondell .......................... 2/209
4,552,137 A * 11/1985 Strauss ........................ 128/864

OTHER PUBLICATIONS

"Hearing Protection Options", EarPlug SuperStore: http://earplugstore.stores.yahoo.net/gennoisprot1.html, Mar. 8, 2010.

* cited by examiner

*Primary Examiner* — Patricia Bianco
*Assistant Examiner* — Victoria J Hicks
(74) *Attorney, Agent, or Firm* — McNees Wallace & Nurick LLC

(57) ABSTRACT

Disclosed is a method and article for protecting an ear by reducing intensity of sound audible to an individual using the article and/or by preventing foreign objects from entering an ear canal of the ear. The article includes a surface configured for removably securing the article to a tragus of the ear and urging the tragus to at least partially cover the ear canal, thereby protecting the ear.

18 Claims, 2 Drawing Sheets

METHOD AND APPARATUS FOR EAR PROTECTION

CROSS-REFERENCE TO RELATED APPLICATIONS

This application claims priority and benefit of U.S. Provisional Patent Application No. 61/209,977 filed Mar. 10, 2010, entitled "EAR MUFFERS," which is hereby incorporated by reference in its entirety.

FIELD OF THE INVENTION

The present invention is directed to a method and article of protecting an ear. More specifically, the present invention is directed to a method and article of protecting an ear by reducing intensity of sound audible to an individual using the article and/or by preventing foreign objects from entering an ear canal of the ear.

BACKGROUND OF THE INVENTION

In general, known ear protection can be in the form of an earplug or an ear muff (for example, a head-phone). The earplugs are inserted into the ear canal of an ear. The earplugs can include a narrower internal portion for insertion into the ear canal and a wider external portion. The wider external portion can be secured by urging a tragus of the ear away from the ear canal. These earplugs can result in foreign objects (for example, oil, dirt, water, and/or bacteria) being introduced into the ear canal. These earplugs suffer from the drawback that they can be uncomfortable. For example, sleeping with the head positioned on its side can result in pressure upon the ear canal. Also, repetitive use of these earplugs may increase risk of infection. Furthermore, these earplugs can be ineffective in certain environments. For example, known earplugs are rated below a noise reduction rating (NRR) of 33. As used herein, the term "noise reduction rating" or "NRR" refers to ANSI S3.19-1974, "American National Standard for the Measurement of Real-Ear Hearing Protector Attenuation and Physical Attenuation of Earmuffs,"specified by 40 C.F.R., Pt. 211, Product Noise Labeling, Subpart B—Hearing Protection Devises.

In general, ear muffs include a large generally circular geometry for covering the entire ear. These ear muffs are large, can be uncomfortable, and can involve complex electronics. The size and shape of these ear muffs prevents comfortable use for sleeping, are visually unappealing, and can be expensive due to the amount of material necessary to effectively protect the ear. In general, known ear muffs are rated below a noise reduction rating of 33. In addition, ear muffs having noise reduction ratings above noise reduction rating 25 can cost hundreds of dollars.

What is needed is a method and article of protecting an ear from noise or external objects that can prevent the introduction of foreign objects into the ear, can reduce the intensity of sound audible to the ear, is comfortable, and is inexpensive.

SUMMARY OF THE INVENTION

One aspect of the present disclosure includes an article for ear protection. The article includes a surface configured for removably securing the article to a tragus of an ear and urging the tragus to at least partially cover an ear canal of the ear, thereby protecting the ear.

Another aspect of the present disclosure includes an article for ear protection. The article includes a first dimension and a second dimension, the first dimension being large enough to cover a tragus of an ear and the second dimension being small enough to be secured within a region formed by an anti-tragus of the ear and an antihelix of the ear. The article further includes a surface configured for removably securing the article to the tragus of the ear and urging the tragus to at least partially cover an ear canal of the ear, thereby protecting the ear. In this embodiment, the surface includes an adhesive, the adhesive being configured to removably secure the article upon the tragus being urged to at least partially cover the ear canal. The at least partial covering of the ear canal protects the ear from entry of foreign objects and reduces intensity of sound audible to the ear.

Another aspect of the present disclosure includes a method of ear protection. The method includes positioning an article, removably securing the article to a tragus of an ear, and urging the tragus of the ear to at least partially cover an ear canal of the ear. In this embodiment, the article includes a surface configured for removably securing the article to the tragus and urging the tragus to at least partially cover the ear canal, thereby protecting the ear.

An advantage of embodiments of the present disclosure includes protecting an ear from noise or external objects.

Another advantage of embodiments of the present disclosure includes reducing the intensity of sound audible to the ear.

Another advantage of embodiments of the present disclosure includes improved comfort in comparison to know techniques for protecting an ear from noise or external objects.

Another advantage of embodiments of the present disclosure includes increased effectiveness of reducing sound or preventing the entry of foreign objects.

Other features and advantages of the present invention will be apparent from the following more detailed description of the preferred embodiment, taken in conjunction with the accompanying drawings which illustrate, by way of example, the principles of the invention.

DETAILED DESCRIPTION OF THE INVENTION

Provided is a method and article of protecting an ear from noise or external objects. The method and article reduce intensity of sound audible to an individual using the article and/or prevent foreign objects from entering an ear canal of the ear.

Embodiments of the present disclosure can protect an ear from noise or external objects, can reduce the intensity of sound audible to the ear, can improve comfort in comparison to know techniques for protecting an ear from noise or external objects, and/or can increase effectiveness of reducing sound or preventing the entry of foreign objects.

Figure 1:
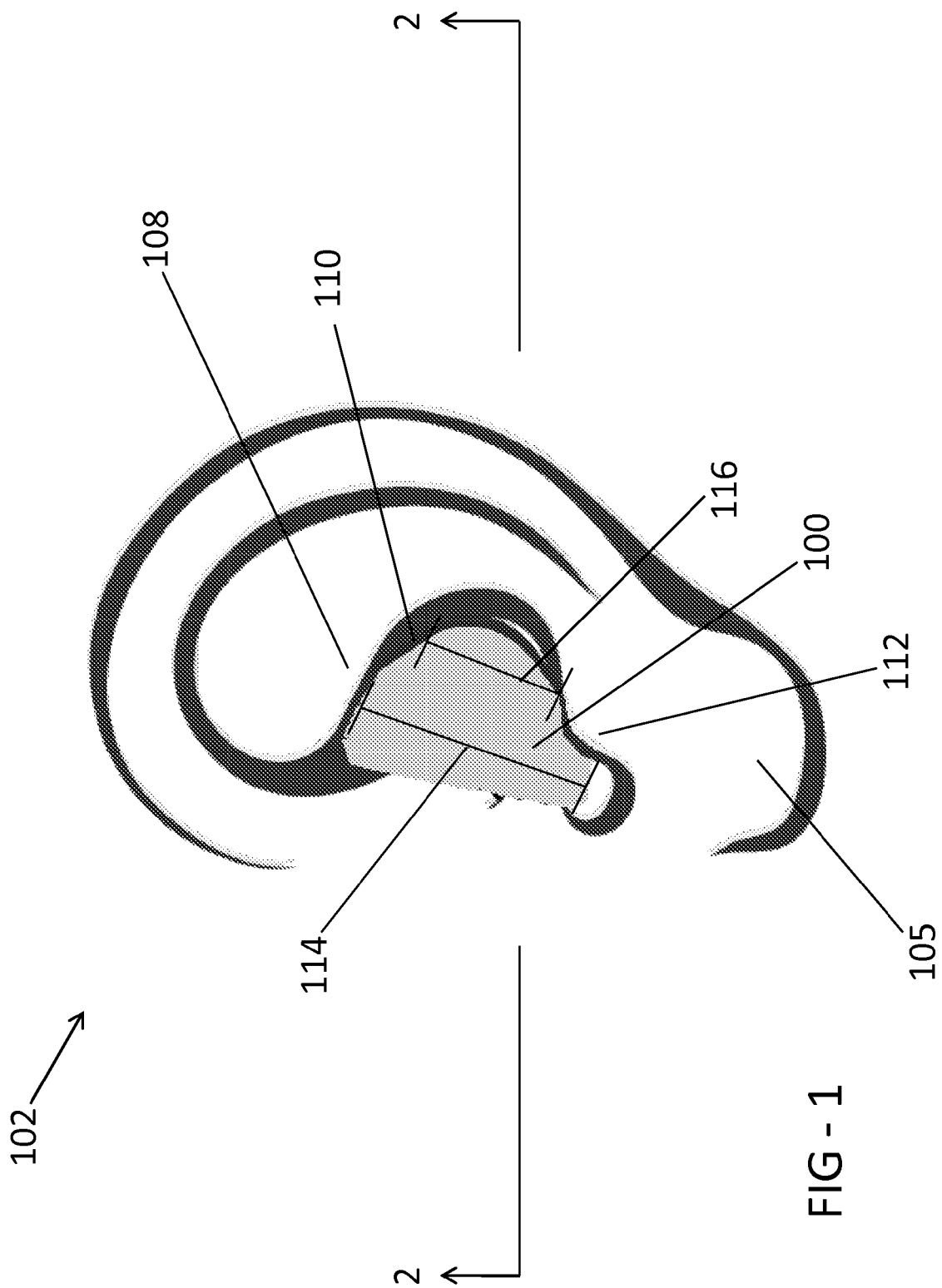
FIG. 1 shows an exemplary embodiment of protective ear article secured to an ear.
Figure 2:
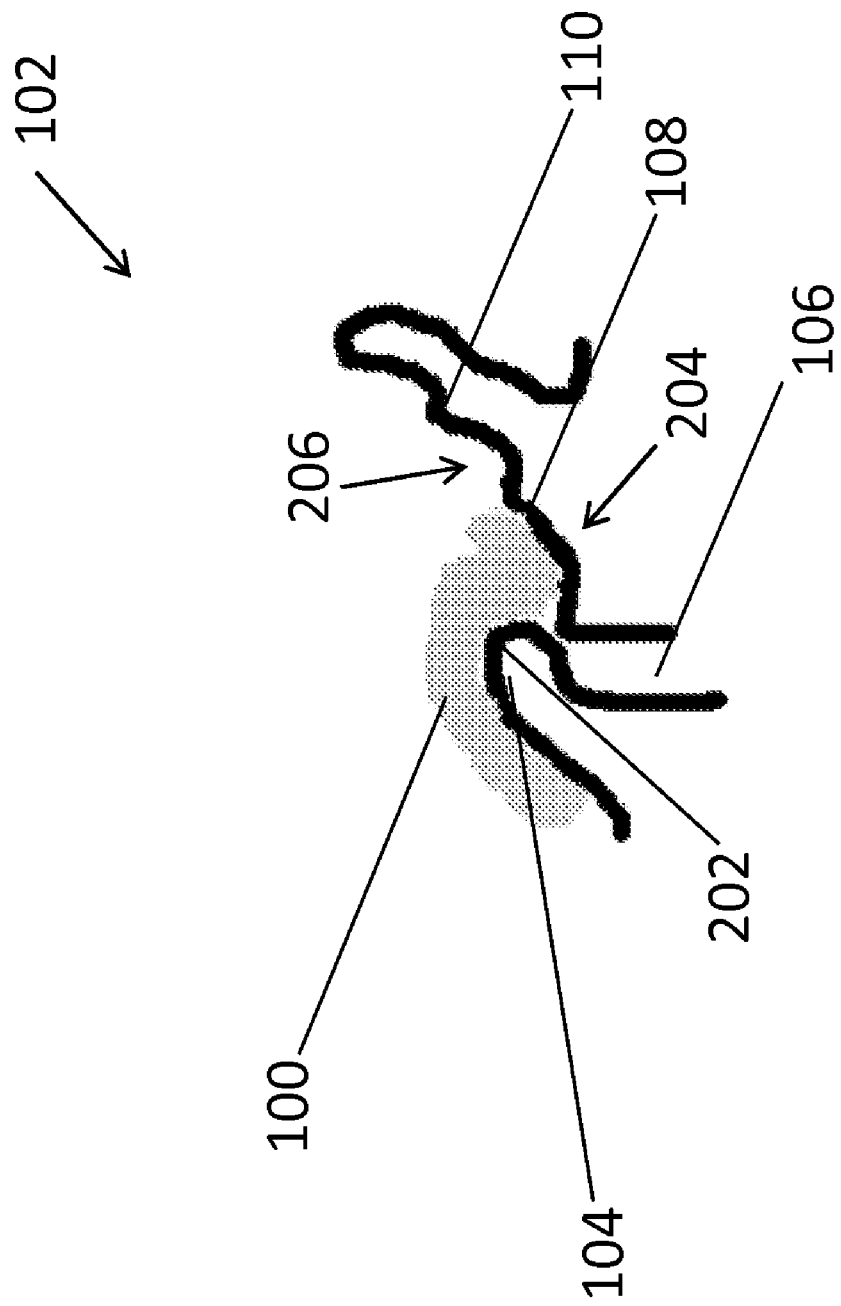
FIG. 2 shows a cross section of FIG. 1 along line 2-2.

FIG. 1 shows an article 100 for ear protection positioned within an ear 102. The ear 102 shown in FIG. 1 includes a tragus 104 (see FIG. 2), an ear canal 106 (see FIG. 2), an antihelix 108, a concha 110, and an antitragus 112. The tragus 104 is a flap of cartilage in the outer ear extending away from the ear canal in its natural resting position. The antihelix 108 is a rounded piece of cartilage inside the outer rim (or helix) of the ear. The concha 110 is a recess in the outer ear bordering the antihelix 108. The antitragus 112 is cartilage in the outer ear bordering an ear lobe 105. The antitragus 112 and the concha 110 form a first region 204 (see FIG. 2). As shown in FIG. 2, in one embodiment, a portion of the article 100 is configured to be removably secured within the first region 204. The antitragus 112 and the antihelix 108 form a second region 206. In another embodiment, a portion of the article 100 is configured to be removably secured within the second region 206.

Referring again to FIG. 1, the article 100 prevents the introduction of foreign objects into the ear 102 and/or reduces the intensity of sound audible to the individual using the article 100 by being positioned and removably secured according to a method of the disclosure. The article 100 can permit use of the article 100 while sleeping without resulting in substantial pressure upon the ear canal 106 while the individual using the article 100 rests on the ear 102. The article 100 includes a first dimension 114 and a second dimension 116. The first dimension 114 is large enough to cover the tragus 104. The article 100 can include rounded edges permitting the article to conform to geometry of the ear 102. In one embodiment, the geometry of the article 100 permits use of the article 100 by substantially all individuals having an ear 102 including the tragus 104 and the ear canal 106. In another embodiment, the geometry of the article 100 can permit use of the article 100 by substantially all individuals having an ear 102 including the tragus 104, the ear canal 106, the antitragus 112, and the antihelix 108. As shown in FIG. 1, the second dimension 116 is configured to be removably secured within the first region 204 formed by the antitragus 112 and the concha 110. For example, the second dimension is small enough to be secured within the first region 204. In another embodiment, the second dimension 116 is configured to be removably secured within the second region formed by the antitragus 112 and the concha 110. For example, the second dimension 116 is small enough to be secured within the second region 206. The article 100 can include other suitable sizes, configurations, and/or geometries.

As shown in FIG. 2, the article 100 includes a surface 202 configured for securing the article 100 to the tragus 104 and urging the tragus 104 to at least partially cover the ear canal 106, thereby protecting the ear 102. Upon securing the article 100 to the tragus 104, the tragus 104 is urged to at least partially cover the ear canal 106. In one embodiment, upon being removably secured, the article 100 urges the tragus 104 to abut the ear canal 106. In one embodiment, the article 100 completely seals the ear canal 106 from the passage of air, water, or other foreign objects. In this embodiment, the article 100 is configured for swimming or other underwater or in-water activities. In a further embodiment, the article 100 urges the tragus 104 to completely seal the ear canal 106.

At least a portion of the surface 202 includes an adhesive configured to removably secure the article 100 upon the tragus 104 being urged to at least partially cover the ear canal 106. The adhesive can directly adhere the article 100 to skin within the ear 102. Surface preparation of the skin to prepare a surface of the ear 102 to receive the article 100 can include cleaning (for example, with soap, water, and/or isopropyl alcohol, etc). The adhesive can be any suitable adhesive. In one embodiment, the adhesive can be a hypoallergenic adhesive. In another embodiment, the adhesive can be waterproof. In a further embodiment, the adhesive can form a water-proof seal permitting the article 100 to substantially prevent water from entering the ear canal 106. In another embodiment, the adhesive can be limited to materials generally recognized as safe or known to be safe on human skin. The adhesive can be configured to be removed by a liquid and/or by being pulled off. In one embodiment, the adhesive can be configured to resist detachment when exposed to force corresponding to a tendency of the tragus 104 to relax to a natural resting position. Additionally or alternatively, the adhesive can be configured to detach at a predetermined application of force less than a predetermined amount of force capable of causing injury upon removal of the article 100.

The article 100 can include any material capable of manipulation and capable of conforming to the shape of the ear 102. In one embodiment, the article 100 includes or is polyvinyl chloride foam. Other suitable polymeric materials can be additional or alternatively included. For example, the article 100 may include or be polyurethane foam, moldable silicon, moldable wax, other suitable materials, or combinations thereof. The material of the article 100 may be selected to further reduce intensity of sound audible to the individual using the article 100. In one embodiment, the material provides sound intensity reduction of at least 20 decibels. In another embodiment, the material and the positioning of the article 100 provides sound intensity reduction of at least 40 decibels. In this embodiment, a portion of the sound intensity reduction is provided by the urging of the tragus 104 to at least partially cover the ear canal 106. Positioning of the article 100 according to the disclosure can result in a noise reduction rating of 34 without being combined with other articles.

The material of the article 100 can be selected to provide any suitable properties. For example, the material can be waterproof, water-resistant, hypoallergenic, generally recognized as safe, compressible, transparent, translucent, or of a predetermined color (for example, varying shades of skin-toned colors). Additionally or alternatively, the article 100 can include a design, text, or other indicia. In one embodiment, the material of the article 100 may be selected to reduce the intensity of sounds having a predetermined frequency. For example, a first material used in the article 100 can be selected to reduce higher frequency sounds and/or a second material used in the article 100 can be selected to reduce lower frequency sounds. Furthermore, the amount of material forming the article 100 can be configured to reduce a predetermined amount of sound audible to the individual using the article 100.

EXAMPLES

In a first example, an article having a circular geometry according to the disclosure was positioned over the tragus and removably secured to a region of the ear formed by the anti-tragus of the ear and the antihelix of the ear. The circular article urged the tragus to cover the ear canal. The circular article reduced intensity of sound audible to an individual using the article and prevented foreign objects from entering an ear canal of the ear. The circular article prematurely became unsecured and was unable to be secured to several ear shapes.

In a second example, an article having a rectangular geometry according to the disclosure was positioned over the tragus and removably secured to a region of the ear formed by the anti-tragus of the ear and the antihelix of the ear. The rectangular article urged the tragus to cover the ear canal. The rectangular article reduced intensity of sound audible to an individual using the article and prevented foreign objects from entering an ear canal of the ear. The rectangular article prematurely became unsecured and was unable to be secured to several ear shapes.

In a third example, an article having a generally trapezoidal geometry and rounded corners according to the disclosure was positioned over the tragus and removably secured to a region of the ear formed by the anti-tragus of the ear and the antihelix of the ear. The generally trapezoidal article urged the tragus to cover the ear canal. The generally trapezoidal article reduced intensity of sound audible to an individual using the article by about 45 decibels resulting in a noise reduction rating of 34 when properly positioned, reduced intensity of sound audible to an individual using the article by about 22 decibels when positioned without urging the tragus to cover the ear canal, and prevented foreign objects from entering an ear canal of the ear. The generally trapezoidal article remained secured until being removed and was able to be secured to a greater range of ear shapes.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An article for ear protection, comprising:
   a surface configured for removably securing the article to a tragus of an ear and urging the tragus to at least partially cover an ear canal of the ear, thereby protecting the ear;
   wherein the surface includes an adhesive, the adhesive being configured to removably secure the article to the ear;
   wherein:
   the surface is generally trapezoidal;
   the article is shaped and configured to be conformable to the shape of the ear and the tragus of the ear, and adapted to overlay the tragus without contacting the ear canal when secured to the ear; and
   wherein:
   the adhesive is adapted to be in contact with the ear in one of a first region formed by an anti-tragus of the ear and an antihelix of the ear, or a second region formed by formed by an anti-tragus of the ear and a concha of the ear, and wherein the adhesive is further adapted to not be in contact with the ear canal when secured to the ear.

2. The article of claim 1, wherein the at least partial covering of the ear canal protects the ear by reducing intensity of sound audible to the ear.

3. The article of claim 2, wherein the at least partial covering of the ear canal reduces the intensity of sound by at least 20 decibels.

4. The article of claim 2, wherein the at least partial covering of the ear canal reduces the intensity of sound by at least 40 decibels.

5. The article of claim 1, wherein the at least partial covering of the ear canal protects the ear from entry of foreign objects.

6. The article of claim 1, wherein the at least partial covering of the ear canal completely seals the ear canal.

7. The article of claim 1, wherein the at least partial covering of the ear canal urges the tragus to abut the ear canal.

8. The article of claim 1, wherein the article comprises a first dimension and a second dimension, the first dimension being large enough to cover the tragus of the ear and the second dimension being small enough to be secured within a region formed by an anti-tragus of the ear and an antihelix of the ear.

9. The article of claim 1, wherein the article comprises a first dimension and a second dimension, the first dimension being large enough to cover the tragus of the ear and the second dimension being small enough to be secured within a region formed by an anti-tragus of the ear and a concha of the ear.

10. The article of claim 1, wherein the article is configured for swimming.

11. A method of ear protection, comprising:
    positioning an article, the article comprising a generally trapezoidal surface configured for removably securing the article to a tragus of an ear and urging the tragus to at least partially cover an ear canal of the ear, thereby protecting the ear;
    removably securing the article to the tragus; and
    urging the tragus to at least partially cover the ear canal;
    wherein the surface includes an adhesive, the adhesive being configured to removably secure the article to the ear;
    wherein:
    the article is shaped and configured to be conformable to the shape of the ear and the tragus of the ear, and adapted to overlay the tragus without contacting the ear canal when secured to the ear; and
    wherein:
    the adhesive is adapted to be in contact with the ear in one of a first region formed by an anti-tragus of the ear and an antihelix of the ear, or a second region formed by formed by an anti-tragus of the ear and a concha of the ear, and wherein the adhesive is further adapted to not be in contact with the ear canal when secured to the ear.

12. The method of claim 11, wherein the at least partial covering of the ear canal protects the ear by reducing intensity of sound audible to the ear.

13. The method of claim 12, wherein the at least partial covering of the ear canal reduces the intensity of sound by at least 20 decibels.

14. The method of claim 13, wherein the at least partial covering of the ear canal reduces the intensity of sound by at least 40 decibels.

15. The method of claim 12, wherein the at least partial covering of the ear canal completely seals the ear canal.

16. The method of claim 12, wherein the at least partial covering of the ear canal urges the tragus to abut the ear canal.

17. The method of claim 11, wherein the at least partial covering of the ear canal protects the ear from entry of foreign objects.

18. An article for ear protection, comprising:
    a first dimension and a second dimension, the first dimension being large enough to cover a tragus of an ear and the second dimension being small enough to be secured within a region formed by an anti-tragus of the ear and an antihelix of the ear;
    a surface configured for removably securing the article to the tragus of the ear and urging the tragus to at least partially cover an ear canal of the ear, thereby protecting the ear;
    wherein the surface includes an adhesive, the adhesive being configured to removably secure the article to the ear;
    wherein:
    the surface is generally trapezoidal;
    the article is shaped and configured to be conformable to the shape of the ear and the tragus of the ear, and adapted to overlay the tragus without contacting the ear canal when secured to the ear; and
    wherein:
    the adhesive is adapted to be in contact with the ear in one of a first region formed by an anti-tragus of the ear and an antihelix of the ear, or a second region formed by formed by an anti-tragus of the ear and a concha of the ear, and wherein the adhesive is further adapted to not be in contact with the ear canal when secured to the ear; and wherein the at least partial covering of the ear canal protects the ear from entry of foreign objects and reduces intensity of sound audible to the ear.

* * * * *